United States Patent [19]

Osborn et al.

[11] Patent Number: 5,112,999
[45] Date of Patent: May 12, 1992

[54] IRIDIUM COMPLEXES, PROCESS FOR THEIR PREPARATION AND THEIR USE

[75] Inventors: John A. Osborn; You P. N. C. Chan, both of Strasbourg, France; Hans-Ulrich Blaser, Ettingen; Felix Spindler, Starrkirch-Wil, both of Switzerland

[73] Assignee: Ciba-Geigy Corporation, Ardsley, N.Y.

[21] Appl. No.: 580,711

[22] Filed: Sep. 11, 1990

[30] Foreign Application Priority Data

Sep. 18, 1989 [CH] Switzerland .................. 3387/89

[51] Int. Cl.$^5$ .................. C07F 15/00; C07F 17/02
[52] U.S. Cl. .................. 556/23; 556/18; 556/19; 556/136; 548/402; 549/206; 549/209; 549/212
[58] Field of Search .................. 556/23, 18, 136, 19; 548/402; 549/206, 209, 212

[56] References Cited

U.S. PATENT DOCUMENTS 4,994,615  2/1991  Spindler et al. .................. 564/304
5,011,995  4/1991  Pugin et al. .................. 564/302

OTHER PUBLICATIONS

J. of Organom. Chem. 173, pp. 231-251 (1979).
J. of Organom. Chem. 133, pp. 231-271 (1977).
J. of Organom. Chem. 118, pp. 205-232 (1976).
J. Chem. Soc. Chem. Commun, 20 pages, 1532-1534 (1986).
J. Soc. Chem. Commun, 12 pages, 869-871 (1990).
Inorganica. Chem. Acta, 73 (1983) 275-279.
J. Chem. Soc. (A), 1971, 2334-2337.
Brunie, J. Mazan, pp. 225-232.
J. Powell et al, CA 68-105339z (1968).
J. Powell et al, CA 68-105340t (1968).
Spindler et al. CA 112-138725c (1990) ef. EP 256,982.
Pugin et al. CA 112-35277d (1990) ef. EP 301,457.

Primary Examiner—Cecilia Shen
Attorney, Agent, or Firm—Kevin T. Mansfield

[57] ABSTRACT

Compounds of general formula I or Ia

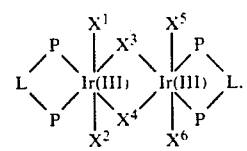

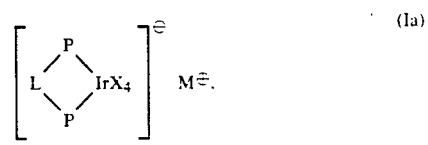

or mixtures thereof, wherein the groups P-L-P are a ligand from the group comprising diphosphine and diphosphinite, in which the secondary phosphine groups or phosphinite groups P are coupled via 2 to 4 C atoms, and which form a 5-, 6- or 7-membered ring with the Ir atoms, X, $X^1$, $X^2$, $X^3$, $X^4$, $X^5$ and $X^6$ independently of the others are Cl, Br or I, or $X^1$ and $X^6$ and H and $X^2$, $X^3$, $X^4$ and $X^5$ independently of the others are Cl, Br or I, or $X^1$ and $X^5$ and H and $X^2$, $X^3$, $X^4$ and $X^6$ independently of the others are Cl, Br or I, and $M^\oplus$ is an alkali metal cation or quaternary ammonium. The compounds are suitable as homogeneous catalysts for the (preferably) asymmetric hydrogenation of N-substituted imines to secondary amines.

18 Claims, No Drawings

IRIDIUM COMPLEXES, PROCESS FOR THEIR PREPARATION AND THEIR USE

The invention relates to iridium-halogen complexes of trivalent iridium which contain diphosphine or diphosphinite ligands, to a process for their preparation and to their use as (in some cases) enantioselective and/or chemoselective catalysts for the hydrogenation of N-substituted imines.

EP-A-0 301 457 and EP-A-0 256 982 disclose the asymmetric hydrogenation of N-substituted imines with mononuclear complexes of monovalent iridium which contain olefin ligands and optically active diphosphine or diphosphinite ligands. Although high yields and enantiomer surpluses are obtained, the catalyst is rapidly deactivated. Carbon double bonds present in the imine are generally hydrogenated as well.

The invention relates to compounds of general formula I or Ia

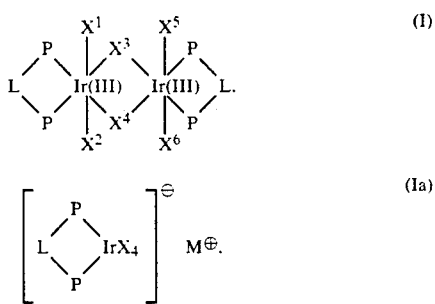

or mixtures thereof, wherein the groups P-L-P are a ligand from the group comprising diphosphine and diphosphinite, in which the secondary phosphine groups or phosphinite groups P are coupled via 2 to 4 C atoms, and which form a 5-, 6- or 7-membered ring with the Ir atoms, X, $X^1$, $X^2$, $X^3$, $X^4$, $X^5$ and $X^6$ independently of the others are Cl, Br or I, or $X^1$ and $X^6$ are H and $X^2$, $X^3$, $X^4$ and $X^5$ independently of the others are Cl, Br or I, or $X^1$ and $X^5$ are H and $X^2$, $X^3$, $X^4$ and $X^6$ independently of the others are Cl, Br or I, and $M^\oplus$ is an alkali metal cation or quaternary ammonium.

The phosphine and phosphinite groups preferably contain two identical or different, especially identical, hydrocarbon radicals having 1 to 20, especially 1 to 12, C atoms.

Preferred compounds of formula I are those in which the secondary phosphine and phosphinite groups contain two identical or different radicals from the group comprising linear or branched $C_1-C_{12}$ alkyl, unsubstituted or $C_1-C_6$ alkyl-substituted $C_5-C_8$ cycloalkyl, phenyl or benzyl, and phenyl or benzyl substituted by $C_1-C_6$ alkoxy (e.g. methoxy), $(C_1-C_6$ alkyl$)_2$N- (e.g. dimethylamino), F, $-SO_3H$, $-SO_3Na$ or $-COO-C_1-C_6$ alkyl (e.g. $-COOCH_3$).

Examples of alkyl, which preferably contains 1 to 6 C atoms, are methyl, ethyl, n-propyl, i-propyl, n-, i-and t-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-substituted phenyl and benzyl are methylphenyl, dimethylphenyl, ethylphenyl and methylbenzyl. Preferred radicals are t-butyl, cyclohexyl, benzyl and especially phenyl.

Preferred compounds of formula I are those in which L in the group P-L-P is linear $C_2-C_4$ alkylene which is unsubstituted or substituted by $C_1-C_6$ alkyl, $C_5-$ or $C_6-$ cycloalkyl, phenyl, naphthyl or benzyl; 1,2- or 1,3-cycloalkylene or -cycloalkenylene, -bicycloalkylene or -bicycloalkenylene having 4 to 10 C atoms, which are unsubstituted or substituted by $C_1-C_6$ alkyl, phenyl or benzyl; cyclic radicals which contain methylene or $C_2-C_4$ alkylidene in the 1- and/or 2-positions or in the 3-position; 1,4-butylene which in the 2,3-position is substituted by

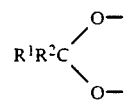

and in the 1,4-positions is unsubstituted or substituted by $C_1-C_6$ alkyl, phenyl or benzyl, $R^1$ and $R^2$ independently of the other being H, $C_1-C_6$ alkyl, phenyl or benzyl; 3,4-or 2,4-pyrrolidinylene or 2-methylenepyrrolidin-4-yl, the N atom of which is substituted by the group $R^3$, $R^3$ being H, $C_1-C_{12}$ alkyl, phenyl, benzyl, $C_1-C_{12}$ alkoxycarbonyl, $C_1-C_8$ acyl or $C_1-C_{12}$ alkylaminocarbonyl; or 1,2-phenylene, 2-benzylene, 1,2-xylylene, 1,8-naphthylene, 2,2'-dinaphthylene or 2,2'-diphenylene, which are unsubstituted or substituted by $C_1-C_4$ alkyl; and P in the group P-L-P is a secondary phosphine group or phosphinite group.

Other preferred compounds of formula I are those in which L in the group P-L-P is the dioxyl radical of a protected mono- or di-saccharide and the groups P are a monovalent secondary phosphine radical.

L in the group P-L-P can contain one or more, e.g. 1 to 3, especially 1 or 2, chiral C atoms and can be in the form of racemates or optical isomers. Especially preferred compounds of formula I are those in which the groups P-L-P are an enantiomer or diastereoisomer of a diphosphine or diphosphinite.

A preferred subgroup of compounds of formula I consists of those in which the group P-L-P has the formula

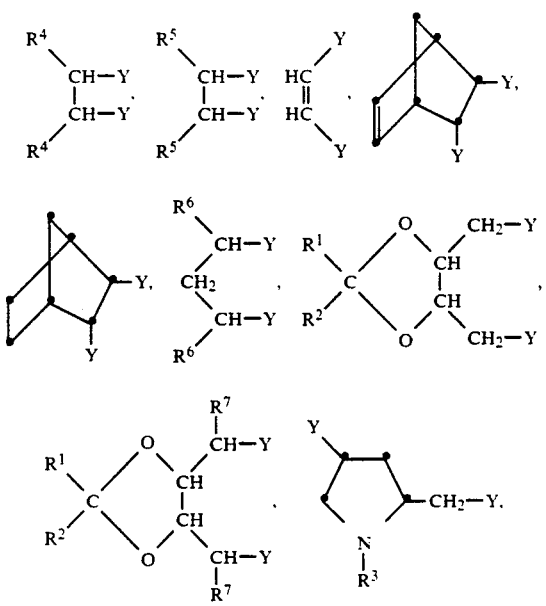

-continued

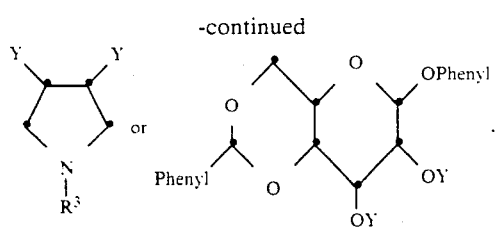

Y being —P(phenyl)$_2$. R$^4$, R$^5$ and R$^6$ being H. C$_1$–C$_4$ alkyl, cyclohexyl, phenyl or benzyl, R$^1$ and R$^2$ being H, C$_1$–C$_4$ alkyl, phenyl or benzyl. R$^7$ being H or C$_1$–C$_4$ alkyl and R$^3$ being H, C$_1$–C$_4$ alkyl, phenyl, benzyl, C$_1$–C$_6$ alkoxy—CO—, C$_1$–C$_6$ alkyl—CO—, phenyl—CO—, naphthyl—CO— or C$_1$–C$_4$ alkylNH—CO—.

Suitable diphosphines and diphosphinites have been described e.g. by H. B. Kagan in Chiral Ligands for Asymmetric Catalysis, Asymmetric Synthesis, volume 5, p. 13-23, Academic Press, Inc., N.Y. (1985).

A few examples are given below (Ph is phenyl):

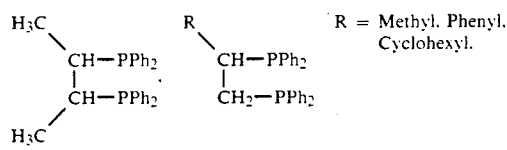

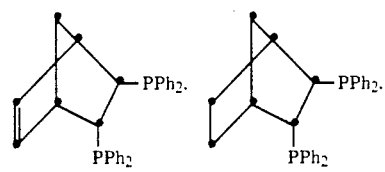

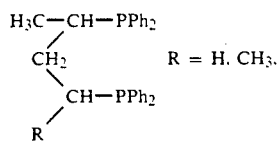

R = H, CH$_3$.

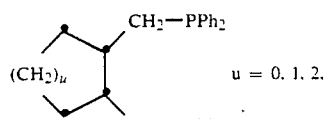

u = 0. 1. 2.

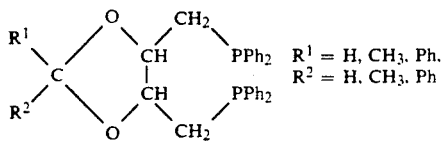

R$^1$ = H, CH$_3$, Ph.
R$^2$ = H, CH$_3$, Ph

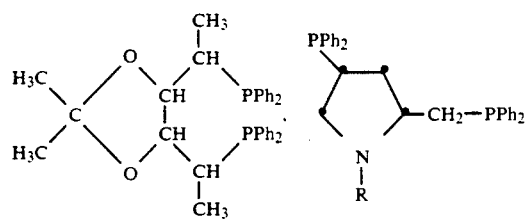

R = —CO$_2$-t-Butyl. —CO-t-Butyl. —CO-Phenyl.
—CONHC$_1$–C$_4$-Alkyl. H.

-continued

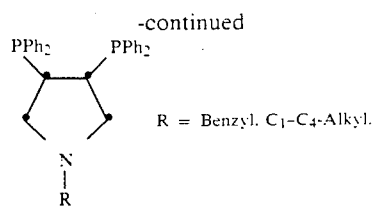

R = Benzyl. C$_1$–C$_4$-Alkyl.

One example of a diphosphinite is the preferred 1-O-phenyl-4,6-O-(R)-benzylidene-2,3-O-bis(diphenylphosphino)-β-D-glucopyranoside of the formula

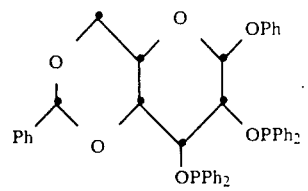

A preferred embodiment consists of compounds of formula I in which the group P-L-P has the formula

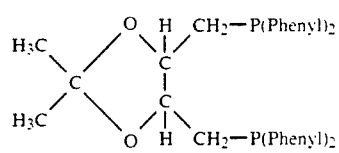

X$^2$ to X$^5$ or X$^1$ to X$^6$ as halogen atoms are especially identical halogen atoms, particularly I. X$^1$ and X$^6$ can be H and X$^2$ to X$^5$ can each be Cl, Br or especially I. X$^1$ and X$^5$ can be H and X$^2$, X$^3$, X$^4$ and X$^6$ can each be Cl, Br or I. Also. X$^1$ to X$^6$ can each be Cl, Br or especially I. The four radicals X in formula Ia are each preferably Cl, Br or especially I. M$^\oplus$ in formula Ia is preferably Li$^\oplus$, Na$^\oplus$, K$^\oplus$ or (C$_1$–C$_6$ alkyl)$_4$N$^\oplus$.

The invention further relates to a process for the preparation of compounds of formula I or Ia or mixtures thereof, which comprises reacting a compound of formula II

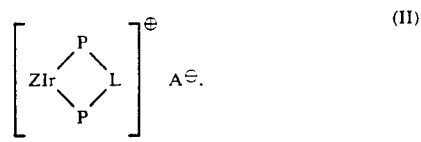

wherein Z is two olefin ligands or one diene ligand, A$^\ominus$ is the anion of an oxygen acid or complex acid and the group P-L-P is as defined above, at elevated temperature, in a ketone as solvent, with an excess of a salt of formula III

wherein M$^\oplus$ is an alkali metal or quaternary ammonium and X is Cl, Br or I, or with mixtures of these salts.

In formula II, Z as an olefin ligand can be e.g. butene, propene or especially ethylene and the diene ligand is preferably an open-chain or cyclic diene in which the diene groups are separated by one or two C atoms. The diene is preferably hexadiene, cyclooctadiene or norbornadiene.

Examples of $A^{\ominus}$ in formula II are $ClO_4^{\ominus}$, $CF_3SO_3^{\ominus}$, $BF_4^{\ominus}$, $B(phenyl)_4^{\ominus}$, $PF_6^{\ominus}$, $SbCl_6^{\ominus}$, $AsF_6^{\ominus}$ and $SbF_6^{\ominus}$.

The iridium compounds of formula II are known or can be prepared by known processes; see e.g. R. Uson et al., Inorg. Chim. Acta 73, p. 275 et seq. (1983); S. Brunie et al., Journal of Organometallic Chemistry, 114 (1976), p. 225–235 and M. Green et al., J. Chem. Soc. (A), p. 2334 et seq. (1971).

The iridium compounds of formula II can be used as isolated compounds. The compounds are conveniently prepared in situ and used direct.

The reaction can be carried out in the temperature range from 40° to 200° C., preferably 50° to 150° C.

Examples of suitable ketones as solvents are acetone, methyl ethyl ketone, methyl isobutyl ketone, cyclopentanone, cyclohexanone and methylcyclohexanone.

The molar ratio of compounds of formula II to compounds of formula III can be e.g. 1:5 to 1:100, preferably 1:10 to 1:50. The reaction is advantageously carried out under an inert gas atmosphere, e.g. a noble gas.

The reaction is generally carried out by dissolving the compound of formula II in a solvent and then adding the compound of formula III. The reaction mixture is subsequently heated for a time, e.g. 2 to 10 hours, and left to cool. To isolate the desired compounds, the solid precipitate is separated off and purified by recrystallization.

Compounds of formula I in which $X^1$ to $X^6$ are each Cl, Br or I can be converted to compounds of formula Ia by reaction with e.g. 1 to 100 mol of a compound of formula III.

With the processes of the invention, mixtures of compounds of formulae I′, I″, I‴ and Ia are generally formed initially:

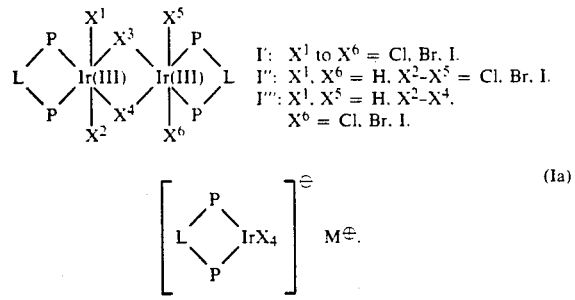

The compounds of formulae I″ and I‴ can be formed due to the presence of water in the reaction mixture as a result of aldol condensation of the ketones used as solvents. The composition of the mixture depends essentially on the choice of diphosphine P-L-P.

If the open-chain ligand P-L-P forms a five-membered ring with the Ir atom, compounds of formula Ia can be formed as the main products, e.g. in a proportion of up to 95%. If the ligand P-L-P forms a six- or seven-membered ring with the Ir atom or if L is a divalent cyclic or polycyclic radical, compounds of formula I″ are formed as the predominant products, e.g. in a proportion of up to 95%. The individual compounds can easily be prepared in pure form by recrystallization.

The compounds of formulae I and Ia, in the form of their mixtures or as pure compounds, are outstanding homogeneous catalysts for the hydrogenation of N-substituted imines under mild reaction conditions. They have a high catalytic activity and it is possible to achieve high yields of up to 100%. A particular advantage is the reusability of the catalyst, which can be recovered after the reaction and shows virtually no loss of activity. Furthermore, these compounds have a good stability to oxygen, so it is not necessary to ensure the complete exclusion of air during the entire hydrogenation process. If the diphosphine or diphosphinite contains chiral C atoms and their enantiomers or diastereoisomers are present in the compounds of formulae I and Ia, the hydrogenation proceeds enantioselectively when using prochiral imines, giving good optical yields.

The compounds of formulae Ia and I″ are surprisingly distinguished by a high chemoselectivity. It has been found that e.g. keto groups, —CN, —NO$_2$, carbon double bonds, N-oxides, aromatic halogen groups and amide groups are not hydrogenated, but the imine group is.

The invention further relates to the use of compounds of formulae I and Ia or mixtures thereof as homogeneous catalysts for the hydrogenation of N-substituted imines and especially for the chemoselective hydrogenation of imines having the afore-mentioned functional groups.

It is preferred to use compounds of formulae I and Ia in which the group P-L-P is an enantiomer or diastereoisomer of a secondary diphosphine or diphosphinite for the asymmetric and in some cases chemoselective hydrogenation of N-substituted prochiral imines.

The invention further relates to a process for the preparation of secondary amines by the hydrogenation of N-substituted imines with hydrogen in the temperature range from −20° to 80° C. and under a hydrogen pressure of $10^5$ to $5 \cdot 10^7$ Pa, in the presence of an iridium complex as homogeneous catalyst, wherein the catalyst used is a compound of formula I or Ia or mixtures thereof.

It is preferred to carry out a process for the preparation of optically active secondary amines, wherein, in formulae I and Ia, the group P-L-P is an enantiomer or diastereoisomer of a secondary diphosphine or diphosphinite and a prochiral N-substituted imine is used.

The process is preferably carried out in the temperature range from −20° to 80° C., especially −20° to 50° C., and preferably under a hydrogen pressure of $2 \cdot 10^5$ to $3 \cdot 10^6$ Pa, especially $8 \cdot 10^5$ to $3 \cdot 10^6$ Pa.

The compounds of formulae I and Ia or mixtures thereof are preferably used in amounts of 0.001 to 10 mol %, especially 0.01 to 10 mol % and in particular 0.1 to 5 mol %, based on the imine.

A preferred method of carrying out the process comprises the additional use of an ammonium or alkali metal chloride, bromide or iodide. The chlorides, bromides and iodides are preferably used in amounts of 0.01 to 200, especially 0.05 to 100 mol % and in particular 0.5 to 50 mol %, based on the compounds of formula I.

The chlorides are the preferred salts. Ammonium is preferably tetraalkylammonium having 1 to 6 C atoms in the alkyl groups and the alkali metal is preferably sodium, lithium or potassium.

The reaction can be carried out in the presence or absence of solvents. Suitable solvents, which can be used by themselves or as a solvent mixture, are especially aprotic solvents, examples being aliphatic and aromatic hydrocarbons such as pentane, hexane, cyclohexane, methylcyclohexane, benzene, toluene and xylene; ethers such as diethyl ether, diethylene glycol dimethyl ether, tetrahydrofuran and dioxane; halogenated hydrocarbons such as methylene chloride, chloroform, 1,1,2,2-tetrachloroethane and chlorobenzene;

esters and lactones such as ethyl acetate, butyrolactone and valerolactone; and acid amides and lactams such as dimethylformamide, dimethylacetamide and N-methyl-pyrrolidone.

According to the invention, the reaction solutions obtained in the preparation of the compounds of formulae I and Ia can also be used direct for the hydrogenation.

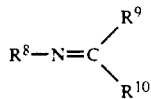
(IV)

wherein $R^8$ is linear or branched $C_1-C_{12}$ alkyl, cycloalkyl having 3 to 8 ring C atoms, heterocycloalkyl bonded via a C atom and having 3 to 8 ring atoms and 1 or 2 heteroatoms from the group comprising O, S and $NR^{11}$, a $C_7-C_{16}$ aralkyl bonded via an alkyl C or $C_1-C_{12}$ alkyl substituted by said cycloalkyl or heterocycloalkyl or heteroaryl, or wherein $R^8$ is $C_6-C_{12}$ aryl or $C_4-C_{11}$ heteroaryl bonded via a ring C atom and having 1 or 2 heteroatoms in the ring, it being possible for $R^8$ to be substituted by $C_1-C_{12}$ alkyl, $C_1-C_{12}$ alkoxy, $C_1-C_{12}$ alkylthio, $C_1-C_6$ halogenoalkyl, —OH, $C_6-C_{12}$ aryl, aryloxy or arylthio, $C_7-C_{16}$ aralkyl, aralkoxy or aralkylthio, secondary amino having 2 to 24 C atoms,

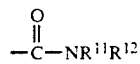

or —COOR$^{11}$, $R^{11}$ and $R^{12}$ independently of the other being $C_1-C_{12}$ alkyl, phenyl or benzyl or $R^{11}$ and $R^{12}$ together being tetra-or penta-methylene or 3-oxapentylene, and it being possible for the aryl radicals in turn to be substituted by $C_1-C_4$ alkyl, alkoxy or alkylthio, —OH, —CONR$^{11}$R$^{12}$ or —COOR$^{11}$;

$R^9$ and $R^{10}$ independently of the other are a hydrogen atom or $C_1-C_{12}$ alkyl or cycloalkyl having 3-8 ring C atoms, which is unsubstituted or substituted by —OH, $C_1-C_{12}$ alkoxy, phenoxy, benzyloxy, secondary amino having 2 to 24 C atoms,

or —COOR$^{11}$, $C_6-C_{12}$ aryl or $C_7-C_{16}$ aralkyl which is unsubstituted or substituted in the same way as $R^8$, —CONR$^{11}$R$^{12}$ or —COOR$^{11}$, wherein $R^{11}$ and $R^{12}$ are as defined above; or $R^8$ is as defined above and $R^9$ and $R^{10}$ together are alkylene having 2 to 5 C atoms, which may be interrupted by 1 or 2 —O—, —S— or —NR$^9$—, and/or is unsubstituted or substituted by =O or the substituents given above for $R^9$ and $R^{10}$ as alkyl, and/or is condensed with benzene, furan, thiophene or pyrrole; or $R^9$ is as defined above and $R^{10}$ is alkylene having 2 to 5 C atoms, which is bonded to $R^8$ and may or may not be interrupted by 1 or 2 —O—, —S— or —NR$^{11}$—, and/or is unsubstituted or substituted by =O or the substituents given above for $R^9$ and $R^{10}$ as alkyl, and/or is condensed with benzene, furan, thiophene or pyrrole.

$R^8$, $R^9$ and $R^{10}$ can be substituted in any positions by identical or different radicals, e.g. by 1 to 5, preferably 1 to 3, substituents.

Suitable substituents for $R^8$ and for $R^9$ and $R^{10}$ are $C_1-C_{12}$, preferably $C_1-C_6$ and especially $C_1-C_4$ alkyl, alkoxy or alkylthio, e.g. methyl, ethyl, propyl, n-, i- and t-butyl, the isomers of pentyl, hexyl, octyl, nonyl, decyl, undecyl and dodecyl, and corresponding alkoxy and alkylthio radicals; $C_1-C_6$ and preferably $C_1-C_4$ halogenoalkyl where halogen is preferably F or Cl, e.g. trifluoro- or trichloro-methyl, difluorochloromethyl, fluorodichloromethyl, 1,1-difluoroeth-1-yl, 1,1-dichloroeth-1-yl, 1,1,1-trichloro- or -trifluoro-eth-2-yl, pentachloroethyl, pentafluoroethyl, 1,1,1-trifluoro-2,2-dichloroethyl, n-perfluoropropyl, i-perfluoropropyl, n-perfluorobutyl, fluoro- or chloro-methyl, difluoro-or dichloro-methyl, 1-fluoro- or -chloro-eth-2-yl or -eth-1-yl, 1-, 2- or 3-fluoro- or -chloro-prop-1-yl, -prop-2-yl or -prop-3-yl, 1-fluoro- or -chloro-but-1-yl, -but-2-yl, -but-3-yl or -but-4-yl, 2,3-dichloroprop-1-yl, 1-chloro-2-fluoroprop-3-yl and 2,3-dichlorobut-1-yl; $C_6-C_{12}$ aryl, aryloxy or arylthio in which aryl is preferably naphthyl and especially phenyl; $C_7-C_{16}$ aralkyl, aralkoxy and aralkylthio in which the aryl radical is preferably naphthyl and especially phenyl and the alkylene radical is linear or branched and contains 1 to 10, preferably 1 to 6 and especially 1-3 C atoms, e.g. benzyl, naphthylmethyl, 1- or 2-phenyleth-1-yl or -eth-2-yl and 1-, 2-or 3-phenyl-prop-1-yl, -prop-2-yl or -prop-3-yl, benzyl being especially preferred; radicals containing the afore-mentioned aryl groups can in turn be mono- or poly-substituted, e.g. by $C_1-C_4$ alkyl, alkoxy or alkylthio, halogen, —OH, —CONR$^{11}$R$^{12}$ or —COOR$^{11}$, $R^{11}$ and $R^{12}$ being as defined; examples are methyl, ethyl, n- and i-propyl, butyl, corresponding alkoxy and alkylthio radicals, F, Cl, Br, dimethyl-, methylethyl- and diethyl-carbamoyl and methoxy-, ethoxy-, phenoxy- and benzyloxy-carbonyl; halogen, preferably F and Cl; secondary amino having 2 to 24, preferably 2 to 12 and especially 2 to 6 C atoms, the secondary amino preferably containing 2 alkyl groups, e.g. dimethyl-, methylethyl-, diethyl-, methylpropyl-, methyl-n-butyl-, di-n-propyl-, di-n-butyl- and di-n-hexyl-amino; —CONR$^{11}$R$^{12}$, wherein $R^{11}$ and $R^{12}$ independently of the other are $C_1-C_{12}$, preferably $C_1-C_6$ and especially $C_1-C_4$ alkyl or $R^{11}$ and $R^{12}$ together are tetra- or penta-methylene or 3-oxapentylene, it being possible for the alkyl to be linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl; or —COOR$^{11}$, wherein $R^{11}$ is $C_1-C_{12}$ and preferably $C_1-C_6$ alkyl which can be linear or branched, e.g. methyl, ethyl, n- and i-propyl, n-, i- and t-butyl and the isomers of pentyl, hexyl, heptyl, octyl, nonyl, decyl, undecyl and dodecyl.

$R^8$, $R^9$ and $R^{10}$ can in particular contain functional groups such as keto groups, —CN, —NO$_2$, carbon double bonds, N—O, aromatic halogen groups and amide groups.

$R^8$ as aryl is preferably unsubstituted or substituted naphthyl and especially phenyl. $R^8$ as heteroaryl is preferably a 5- or 6-membered ring having 1 or 2 identical or different heteroatoms, especially O, S or N, which preferably contains 4 or 5 C atoms and can be condensed with benzene. Examples of heteroaromatics from which $R^8$ can be derived are furan, pyrrole, thiophene, pyridine, pyrimidine, indole and quinoline.

$R^8$ as heteroaryl-substituted alkyl is preferably derived from a 5- or 6-membered ring having 1 or 2 identical or different heteroatoms, especially O, S or N, which preferably contains 4 or 5 C atoms and can be condensed with benzene. Examples of heteroaromatics are furan, pyrrole, thiophene, pyridine, pyrimidine, indole and quinoline.

$R^8$ as heterocycloalkyl or heterocycloalkyl-substituted alkyl preferably contains 4 to 6 ring atoms and 1 to 2 identical or different heteroatoms from the group comprising O, S and $NR^{11}$. It can be condensed with benzene. It can be derived e.g. from pyrrolidine, tetrahydrofuran, tetrahydrothiophene, indane, pyrazolidine, oxazolidine, piperidine, piperazine or morpholine.

$R^8$, $R^9$ and $R^{10}$ as alkyl are preferably unsubstituted or substituted $C_1$-$C_6$ and especially $C_1$-$C_4$ alkyl which can be linear or branched. Examples are methyl, ethyl, i- and n-propyl, i-, n- and t-butyl and the isomers of pentyl, hexyl, heptyl, octyl, nonyl, decyl, undecyl and dodecyl.

$R^8$, $R^9$ and $R^{10}$ as unsubstituted or substituted cycloalkyl preferably contain 3 to 6 and especially 5 or 6 ring C atoms. Examples are cyclopropyl, cyclobutyl, cyclopentyl, cyclohexyl, cycloheptyl and cyclooctyl.

$R^8$, $R^9$ and $R^{10}$ as aryl are preferably unsubstituted or substituted naphthyl and especially phenyl. $R^8$, $R^9$ and $R^{10}$ as aralkyl are preferably unsubstituted or substituted phenylalkyl having 1-10, preferably 1 to 6 and especially 1 to 4 C atoms in the alkylene, it being possible for the alkylene to be linear or branched. Examples are especially benzyl and also 1-phenyleth-1-yl, 2-phenyleth-1-yl, 1-phenylprop-1-yl, 1-phenylprop-2-yl, 1-phenylprop-3-yl, 2-phenylprop-1-yl, 2-phenylprop-2-yl and 1-phenylbut-4-yl. In $R^9$ and $R^{10}$ as $-CONR^{11}R^{12}$ and $-COOR^{11}$, $R^{11}$ and $R^{12}$ are preferably $C_1$-$C_6$ and especially $C_1$-$C_4$ alkyl or $R^{11}$ and $R^{12}$ together are tetramethylene, pentamethylene or 3-oxapentylene. Examples of alkyl have been mentioned above.

$R^9$ and $R^{10}$ together or $R^{10}$ as alkylene bonded to $R^8$ are preferably interrupted by 1 $-O-$, $-S-$ or $-NR^{11}-$, preferably $-O-$. $R^9$ and $R^{10}$ together or $R^{10}$ bonded to $R^8$ preferably form a 5- or 6-membered ring with the C atom or with the $-N=C-$ group to which they are bonded. The substituents have the preferred meanings mentioned above. As condensed alkylene, $R^9$ and $R^{10}$ together or $R^{10}$ bonded to $R^8$ are preferably alkylene condensed with benzene or pyridine. Examples of alkylene are ethylene, 1,2- or 1,3-propylene, 1,2-, 1,3- or 1,4-butylene, 1,5-pentylene and 1,6-hexylene. Examples of interrupted alkylene or alkylene substituted by $=O$ are 2-oxa-1,3-propylene, 2-oxa-1,4-butylene, 2-oxa- or 3-oxa-1,5-pentylene, 3-thia-1,5-pentylene, 2-thia-1,4-butylene, 2-thia-1,3-propylene, 2-methylimino-1,3-propylene, 2-ethylimino-1,4-butylene, 2- or 3-methylimino-1,5-pentylene, 1-oxo-2-oxa-1,3-propylene, 1-oxo-2-oxa-1,4-butylene, 2-oxo-3-oxa-1,4-butylene and 1-oxa-2-oxo-1,5-pentylene.

Examples of condensed alkylene are

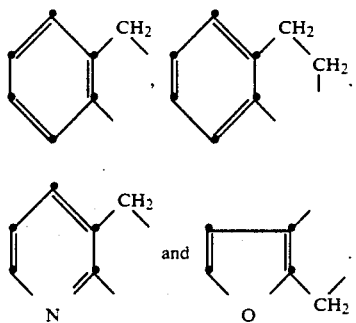

Examples of condensed and interrupted alkylene and alkylene which is unsubstituted or substituted by $=O$ are

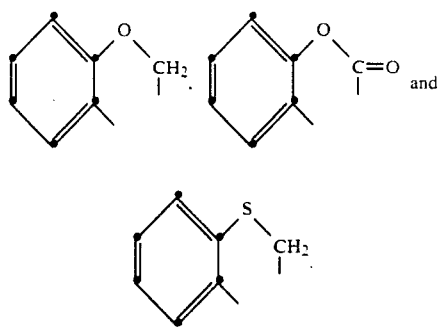

In a preferred group, $R^8$ in formula IV is 2,6-dimethylphen-1-yl or 2-methyl-6-ethylphen-1-yl, $R^9$ is methyl and $R^{10}$ is methoxymethyl.

Another preferred group consists of prochiral imines in which $R^9$ and $R^{10}$ are different from one another and are not hydrogen.

Imines of formula IV are known or can be prepared by known processes from aldehydes or ketones and primary amines. In one embodiment of the process, the imines of formula IV can also be prepared in situ.

The amines which can be prepared according to the invention are biologically active substances or intermediates for the preparation of such substances, especially in the field of the preparation of pharmaceuticals and agrochemicals. Thus e.g. o,o-dialkylarylketamine derivatives, especially those containing alkyl and/or alkoxyalkyl groups, are active as fungicides and especially as herbicides. The derivatives can be amine salts, acid amides, e.g. of chloroacetic acid, tertiary amines and ammonium salts (see e.g. EP-A-0 077 755 and EP-A-0 115 470).

The following Examples illustrate the invention in greater detail.

PREPARATORY EXAMPLES

Example 1

Under an argon atmosphere, 600 mg (0.67 mmol) of $[Ir(COD)(DIOP)]BF_4$ are dissolved in 10 ml of acetone and 900 mg (6.7 mmol) of LiI are added. This reaction mixture is stirred for 20 h at the reflux temperature, producing a yellow precipitate. The reaction solution is cooled to room temperature and centrifuged. The yellow product is separated off, washed with 5 ml of acetone and then dried. The solid residue is extracted with 10 ml of $CH_2Cl_2$. The methylene chloride phase is left to stand at room temperature and white crystals of LiI precipitate out. After filtration, 10 ml of diethyl ether are added to the yellow solution and 317 mg of pale yellow crystals are formed within one day. Further recrystallization of the mother liquor gives a total of 375 mg (58%) of $[Ir(DIOP)HI_2]_2$.

Elemental analysis, found (calculated): C 39.7 (39.38), H 3.7 (3.52), P 7.4 (6.55), I 26.3 (26.80).

$^1H$ NMR ($CD_2Cl_2$, 200 MHz, hydride region): $-16.2$ ppm (t, $^2J_{PH}$: 11 Hz), $-11.7$ ppm (t, $^2J_{PH}$: 11 Hz).

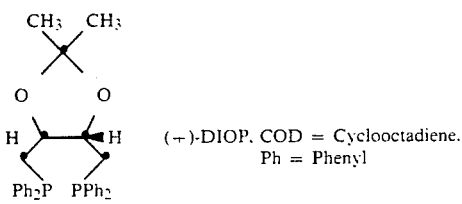

(+)-DIOP. COD = Cyclooctadiene.
Ph = Phenyl

Example 2

Analogously to Example 1, 340 mg (64%) of [Ir(BDPP)HI$_2$]$_2$ are obtained using 500 mg (0.6 mmol) of [Ir(COD)(BDPP)]BF$_4$.

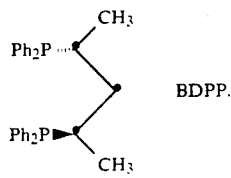

BDPP.

Example 3

Analogously to Example 1, 283 mg (52%) of [Ir(NORPHOS)HI$_2$]$_2$ are obtained using 510 mg (0.6 mmol) of [Ir(COD)(NORPHOS)]BF$_4$.

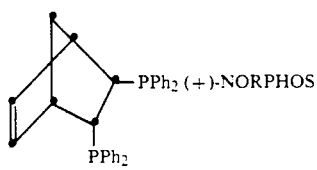

Example 4

Analogously to Example 1, 180 mg (10%) of [Ir(CHIRAPHOS)I$_3$]$_2$ are obtained from 1.5 g (1.85 mmol) [Ir(COD)(CHIRAPHOS)]BF$_4$ with 8 g (60 mmol) of LiI.

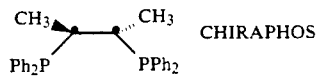

CHIRAPHOS

Elemental analysis (found/calculated in %): C 33.8/33.65; H 2.9/2.82; I 37.0 (38.1); P 6.2/6.2.

Example 5

A solution of 150 mg (0.19 mmol) of [Ir(COD)(R-PROPHOS)]BF$_4$ in 3 ml of acetone is reacted with 400 g (2.98 mmol) of LiI at the reflux temperature for 2 hours. After a further 2 hours at room temperature, 10 ml of diethyl ether are added to the deep red solution, resulting in the formation of two phases and the precipitation of white LiI crystals. The mixture is filtered and the red oily phase is decanted. This is then dissolved in 8 ml of a tetrahydrofuran/diethyl ether mixture (5:3) and, after standing for 3 days at room temperature, 40 mg of microcrystalline orange [Ir(R-PROPHOS)I$_4$]Li are obtained. After filtration, the mother liquor is left to stand for one week to give a further 30 mg of the salt (yield: 33%).

COD = Cyclooctadiene
Ph = Phenyl

R-PROPHOS = Ph$_2$P—CH$_2$—CH(CH$_3$)—PPh$_2$.

Example 6

[Ir(COD)(DPPE)]BF$_4$ (700 mg; 1.12 mmol) is dissolved in 10 ml of acetone, LiI (5.0 g; 37 mmol) is added and the mixture is then stirred for 3 hours at the reflux temperature. 10 ml of acetone are added to the red reaction solution formed. The resulting solution is cooled to room temperature and, after standing for 2 days, [Ir(DPPE)I$_4$]Li is isolated. The mother liquor is left to stand for 5 days to give a further 200 mg of the red salt.

$^1$H NMR: 8.30 ppm and 7.18 ppm, m (20H); 3.04 ppm, d, J=16 Hz (4H).

DPPE=1,2-bis(diphenylphosphino)ethane.

Example 7

Example 6 is repeated, except that the mixture is refluxed for 20 hours. After standing for 2 days, 580 mg of [Ir(DPPE)I$_4$]Li are obtained.

15 ml of methanol are added to the mother liquor. The crystalline precipitate formed consists of 283 mg of [Ir(DPPE)HI$_2$]$_2$.

APPLICATION EXAMPLES

Example 8

15 mg (7.9·10$^{-3}$ mmol) of the compound of Example 1 are dissolved in 2.5 ml of methylene chloride and 7.5 ml of tetrahydrofuran (THF). 1.5 g (7.84 mmol) of N-(2,6-dimethylphen-1-yl)methylmethoxymethylketimine are added and the solution is then transferred to an autoclave thermostated at 30° C. 2·10$^6$ Pa of hydrogen pressure is applied in each of three flushing cycles. Finally, 4·10$^6$ Pa of hydrogen pressure is applied, with stirring. The hydrogenation is followed by recording the hydrogen uptake. After 11 h, the reaction is complete, the hydrogen pressure is released and the solution is transferred to a flask. The solvent is removed on a rotary evaporator. The residue is distilled under high vacuum to leave a yellow precipitate, which is identified as [Ir(DIOP)HI$_2$]$_2$. (2,6-Dimethylphen-1-yl)(1-methoxyprop-2-yl)amine is obtained with a yield of >99% and an optical yield ee=54% (S configuration).

The optical yield is determined by polarimetry ([α]$^{20}_{365}$=−130.6°, C=3 in hexane, S enantiomer).

Examples 9-13

The procedure is analogous to Example 8. The reaction conditions and yields are given in Table 1. The reaction temperature is 25° C. in Examples 8-11 and 30° C. in Example 12.

TABLE 1

| Example | Catalyse | Molar ratio imine:catalyst | H$_2$-pressure (10$^6$ Pa) | Solvent | Reaction time (h) | Yield (%) | ee (configuration) |
|---|---|---|---|---|---|---|---|
| 9 | Example 1 | 2000 | 10 | THF/CH$_2$CCl$_2$(3:1) | 40 | 99 | 63(S) |

TABLE 1-continued

| Example | Catalyse | Molar ratio imine: catalyst | H₂-pressure (10⁶ Pa) | Solvent | Reaction time (h) | Yield (%) | ee (configuration) |
|---|---|---|---|---|---|---|---|
| 10 | Example 2 | 100 | 2.5 | CH₂Cl₂ | 24 | 99 | 29(R) |
| 11 | Example 3 | 100 | 2.5 | CH₂Cl₂ | 24 | 100 | 43(R) |
| 12 | Example 4 | 380 | 4 | CH₂Cl₂ | 40 | 95 | 42(R) |
| 13¹ | Example 1 | 500 | 4 | THF/CH₂CCl₂(3:1) | 6 | 100 | 62(S) |

¹Also 1.58 · 10² mmol of LiCl.

Example 14

13.6 g (1.23·10⁻² mmol) of [Ir(DPPE)I₄]Li are dissolved in 10 ml of a tetrahydrofuran/CH₂Cl₂ solvent mixture (3:1) under inert gas (argon). 0.28 g (1.23 mmol) of N-(4-nitrophenyl) benzylideneimine is then introduced. The substrate/catalyst solution is transferred to a 50 ml steel autoclave. After flushing with hydrogen gas, 2.5·10⁶ Pa of hydrogen pressure is applied and the autoclave is heated to 30° C. in an oil bath.

After 2 h, the reaction is comlete and the reaction solution is analyzed. N-(4-Nitrophenyl)benzylamine is obtained in 100% yield.

Examples 15 to 18

The imines given in Table 2 are hydrogenated analogously to Example 14, except that 20 ml of solvent are used.

TABLE 2

Hydrogenation of 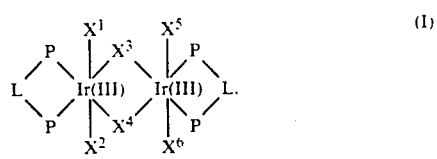

| Example | R | Reaction time (h) | Yield (%) |
|---|---|---|---|
| 15 | —NO₂ | 7 | 100 |
| 16 | —C(O)—CH₃ | 15 | 100 |
| 17 | 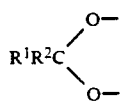 | 15 | 100 |
| 18 | —CN | 20 | 99.5 |

Example 19

5.6 g of [Ir(COD)Cl]₂, 8.6 mg of (+)-DIOP and 58.4 mg of (n-butyl)₄NI are dissolved in 7.5 ml of tetrahydrofuran in a Schlenk vessel under an argon atmosphere and the solution is then transferred to a 50 ml steel autoclave with a steel capillary. The solution is stirred for 6 hours at 60° C. and then cooled to room temperature, after which a solution of 1.5 g of N-(2,6-dimethylphen-1-yl)methylmethoxymethylketimine in 2.5 ml of methylene chloride is added and hydrogenation is carried out according to Example 8. After a hydrogenation time of 16 h, the desired amine is isolated with a conversion of >99% and an optical yield of 54.7%.

What is claimed is:

1. A compound of formula I or Ia

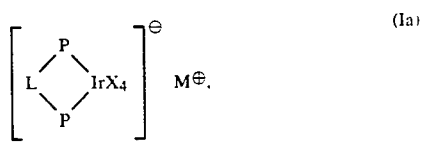

or mixtures thereof, wherein the groups P-L-P are a ligand selected from the group consisting of diphosphine and diphosphinite, in which the secondary phosphine groups or phosphinite groups P are coupled via 2 to 4 C atoms, and which form a 5-, 6- or 7-membered ring with the Ir atoms, X, X¹, X², X³, X⁴, X⁵ and X⁶ independently of the others are Cl, Br or I, or X¹ and X⁶ are H and X², X³, X⁴ and X⁵ independently of the others are Cl, Br or I, or X¹ and X⁵ are H and X², X³, X⁴ and X⁶ independently of the others are Cl, Br or I, and M⊕ is an alkali metal cation or quaternary ammonium.

2. A compound according to claim 1, wherein the secondary phosphine and phosphinite groups contain two identical or different radicals selected from the group consisting of linear or branched C₁-C₁₂ alkyl, unsubstituted or C₁-C₆ alkyl-substituted C₅-C₈ cycloalkyl, phenyl or benzyl, and phenyl or benzyl substituted by C₁-C₆ alkoxy, (C₁-C₆ alkyl)₂N-, F, -SO₃H, -SO₃Na or —COO—C₁-C₆ alkyl.

3. A compound according to claim 2, wherein the secondary phosphine and phosphinite groups each contain two phenyl groups.

4. A compound according to claim 1, wherein L in the group P-L-P is linear C₂-C₄ alkylene which is unsubstituted or substituted by C₁-C₆ alkyl, C₅- or C₆-cycloalkyl, phenyl, naphthyl or benzyl; 1,2- or 1,3-cycloalkylene or -cycloalkenylene, -bicyloalkylene or -bicyloalkenylene having 4 to 10 C atoms, which are unsubstituted or substituted by C₁-C₆ alkyl, phenyl or benzyl; cyclic radicals which contain methylene or C₂-C₄ alkylidene in the 1- and/or 2-positions or in the 3-position; 1,4-butylene which in the 2,3-position is substituted by $$R^1R^2C\begin{matrix}\diagup O- \\ \diagdown O-\end{matrix}$$

and in the 1,4-positions is unsubstituted or substituted by C₁-C₆ alkyl, phenyl or benzyl, R¹ and R² independently of the other being H, C₁-C₆ alkyl, phenyl or benzyl; 3,4- or 2,4-pyrrolidinylene or 2-methylenepyrrolidin-4-yl, the N atom of which is substituted by the group $R^3$, $R^3$ being H, $C_1-C_{12}$ alkyl, phenyl, benzyl, $C_1-C_{12}$ alkoxycarbonyl, $C_1-C_8$ acyl or $C_1-C_{12}$ alkylaminocarbonyl; or 1,2-phenylene, 2-benzylene, 1,2-xylylene, 1,8-naphthylene, 2,2'-dinaphthylene or 2,2'-diphenylene, which are unsubstituted or substituted by $C_1-C_4$ alkyl; and P in the group P-L-P is a secondary phosphine group or phosphinite group.

5. A compound according to claim 1, wherein L in the group P-L-P is the dioxyl radical of a protected mono- or di-saccharide and the groups P are a monovalent secondary phosphine radical.

6. A compound according to claim 1, wherein the groups P-L-P are an enantiomer or diastereoisomer of a diphosphine or diphosphinite.

7. A compound according to claim 1, wherein the group P-L-P has the formula

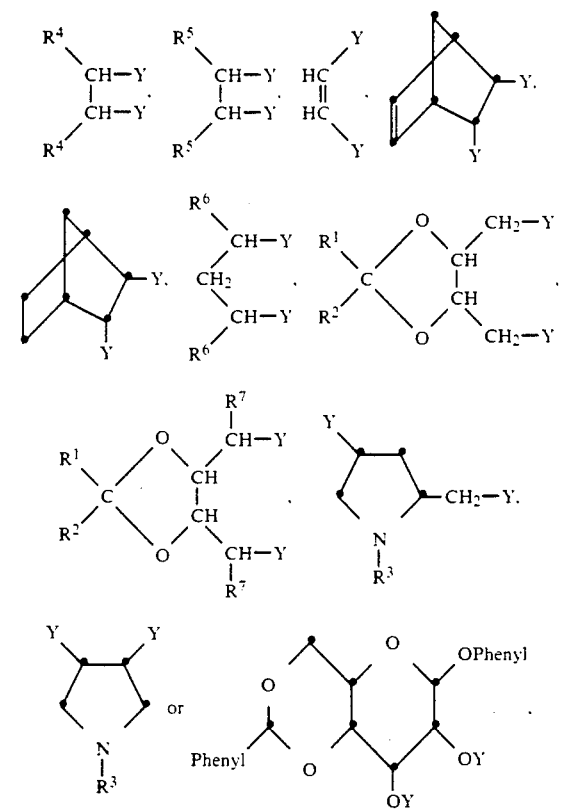

Y being —P(phenyl)$_2$, $R^4$, $R^5$ and $R^6$ being H, $C_1-C_4$ alkyl, cyclohexyl, phenyl or benzyl, $R^1$ and $R^2$ being H, $C_1-C_4$ alkyl, phenyl or benzyl, $R^7$ being H or $C_1-C_4$ alkyl and $R^3$ being H, $C_1-C_4$ alkyl, phenyl, benzyl, $C_1-C_6$ alkoxy—CO—, $C_1-C_6$ alkyl—CO—, phenyl—CO—, naphthyl—CO— or $C_1-C_4$ alkyl-NH—CO—.

8. A compound according to claim 7, wherein the group P-L-P has the formula

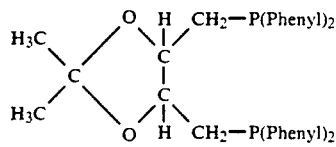

9. A compound according to claim 1, wherein, in formula I, $X^1$ and $X^6$ are H and $X^2$ to $X^5$ are each Cl, Br or I, or $X^1$ and $X^5$ are H and $X^2$, $X^3$, $X^4$ and $X^6$ are each Cl, Br or I.

10. A compound according to claim 9, wherein, in formula I, $X^2$ to $X^5$ or $X^2$, $X^3$, $X^4$ and $X^6$ are each I.

11. A compound according to claim 1, wherein, in formula I, $X^1$ to $X^6$ are each Cl, Br or I.

12. A compound according to claim 11, wherein, in formula I, $X^1$ to $X^6$ are each I.

13. A compound according to claim 1, wherein, in formula Ia, the four radicals X are Cl, Br or I.

14. A compound according to claim 13, wherein, in formula Ia, the four radicals X are each I.

15. A compound according to claim 1, wherein, in formula Ia, $M^\oplus$ is $Li^\oplus$, $Na^\oplus+$, $K^\oplus$ or $(C_1-C_6$ alkyl$)_4N^\oplus$.

16. A process for the preparation of a compound of formula I or Ia or mixtures thereof according to claim 1, which comprises reacting a compound of formula II

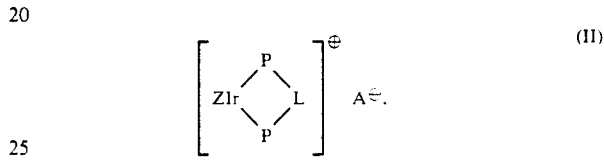

wherein Z is two olefin ligands or one diene ligand, $A^\ominus$ is $ClO_4^\ominus$, $CF_3SO_3^\ominus$, $BF_4^\ominus$, $B(phenyl)_4^\ominus$, $PF_6^\ominus$, $SbCl_6^\ominus$, $AsF_6$ or $SbF_6^\ominus$ and the group P-L-P is as defined in claim 1, at elevated temperature, in a ketone as solvent, with an excess of a salt of formula III

wherein $M^\oplus$ is an alkali metal or quaternary ammonium cation and X is Cl, Br or I, or with mixtures of these salts.

17. A process for the preparation of secondary amines by the hydrogenation of N-substituted imines with hydrogen in the temperature range from $-20°$ to $80°$ C. and under a hydrogen pressure of $10^5$ to $5 \cdot 10^7$ Pa, in the presence of an iridium complex as homogeneous catalyst, wherein the catalyst used is a compound of formula I or Ia or mixtures thereof, according to claim 1.

18. A process according to claim 17 for the preparation of optically active secondary amines wherein, in formulae I and Ia, the group P-L-P is an enantiomer or diastereoisomer of a secondary diphosphine or diphosphinite and a prochiral N-substituted imine of the formula IV

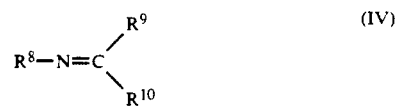

wherein $R^8$ is linear or branched $C_1-C_{12}$alkyl, cycloalkyl having 3 to 8 ring C atoms, heterocycloalkyl bonded via a C atom and having 3 to 8 ring atoms and 1 or 2 heteroatoms selected from the group consisting of O, S and $NR^{11}$, a $C_7-C_{16}$aralkyl bonded via an alkyl C or $C_1-C_{12}$alkyl substituted by said cycloalkyl or heterocycloalkyl or heteroaryl, or wherein $R^8$ is $C_6-C_{12}$aryl or $C_4-C_{11}$heteroaryl bonded via ring C atom and having 1 or 2 heteroatoms in the ring, and $R^8$ can be substituted by $C_1-C_{12}$alkyl, $C_1-C_{12}$alkoxy, $C_1-C_{12}$alkylthio, $C_1-C_6$halogenoalkyl, —OH, $C_6-C_{12}$aryl, aryloxy or arylthio, $C_7$-$C_{16}$aralkyl, aralkoxy or aralkylthio, secondary amino having 2 to 24 C atoms, —$CONR^{11}R^{12}$ or —$COOR^{11}$, $R^{11}$ and $R^{12}$ independently of the other being $C_1$-$C_{12}$alkyl, phenyl or benzyl or $R^{11}$ and $R^{12}$ together being tetra- or penta-methylene or 3-oxapentylene, and said aryl radicals can in turn be substituted by $C_1$-$C_4$alkyl, alkoxy or alkylthio, —OH, —$CONR^{11}R^{12}$ or —$COOR^{11}$; $R^9$ and $R^{10}$ independently of the othr are a hydrogen atom or $C_1$-$C_{12}$alkyl or cycloalkyl having 3-8 ring C atoms, which is unsubstituted or substituted by —OH, $C_1$-$C_{12}$alkoxy, phenoxy, benzyloxy, secondary amino having 2 to 24 C atoms, —$CONR^{11}R^{12}$ or —$COOR^{11}$, $C_6$-$C_{12}$aryl or $C_7$-$C_{16}$aralkyl which is unsubstituted or substituted in the same way as $R^8$, —$CONR^{11}R^{12}$ or —$COOR^{11}$, wherein $R^{11}$ and $R^{12}$ are as defined above; or $R^8$ is as defined above and $R^9$ and $R^{10}$ together are alkylene having 2 to 5 C atoms, which may be interrupted by 1 or 2 —O—, —S— or —$NR^9$—, and/or is unsubstituted or substituted by =O or the substituents given above for $R^9$ and $R^{10}$ as alkyl, and/or is condensed with benzene, furan, thiophene or pyrrole; or $R^9$ is as defined above and $R^{10}$ is alkylene having 2 to 5 C atoms, which is bonded to $R^8$ and may or may not be interrupted by 1 or 2 —O—, —S— or —$NR^{11}$—, and/or is unsubstituted or substituted by =O or the substituents given above for $R^9$ and $R^{10}$ as alkyl, and/or is condensed with benzene, furan, thiophene or pyrrole is used.

* * * * *